(12) United States Patent
Bottani et al.

(10) Patent No.: US 6,485,626 B1
(45) Date of Patent: Nov. 26, 2002

(54) MULTIPLE CAPILLARY ELECTROPHORESIS DEVICES WITH DETECTION IN CAPILLARY OUTPUT

(75) Inventors: Samuele Bottani, Paris (FR); Rainer Siebert, Les Clayes-sous-Bois (FR); Hans Rebscher, Mannheim (DE); Maurice Cohen-Solal, Fontenay-aux-Roses (FR); Luc Valentin, Bures (FR)

(73) Assignee: Centre National de la Recherche Scientifique (FR)

( * ) Notice: Subject to any disclaimer, the term of this patent is extended or adjusted under 35 U.S.C. 154(b) by 0 days.

(21) Appl. No.: 09/423,925

(22) PCT Filed: Mar. 11, 1999

(86) PCT No.: PCT/FR99/00538

§ 371 (c)(1),
(2), (4) Date: Jan. 31, 2000

(87) PCT Pub. No.: WO99/46589

PCT Pub. Date: Sep. 16, 1999

(30) Foreign Application Priority Data

Mar. 11, 1998 (FR) .............................................. 98 03100

(51) Int. Cl.[7] ...................... G01N 27/26; G01N 27/447
(52) U.S. Cl. ...................... 204/603; 204/451; 204/601
(58) Field of Search ................................. 204/451–455, 204/601–603

(56) References Cited

U.S. PATENT DOCUMENTS

| 5,092,972 | A | * | 3/1992 | Ghowsi |
| 5,151,164 | A | * | 9/1992 | Blanchard et al. |
| 5,358,618 | A | * | 10/1994 | Ewing et al. |
| 5,439,578 | A | * | 8/1995 | Dovichi et al. |
| 5,529,679 | A | * | 6/1996 | Takahashi et al. |
| 5,858,187 | A | * | 1/1999 | Ramsey et al. |

FOREIGN PATENT DOCUMENTS

WO         WO 98/26280         6/1998

* cited by examiner

Primary Examiner—T. Tung
(74) Attorney, Agent, or Firm—Blakely Sokoloff Taylor & Zafman (57) ABSTRACT

The invention concerns a multiple capillary electrophoresis device comprising a plurality of juxtaposed capillaries, means for generating inside the capillaries an electric field ensuring electrophoretic migration, at least one source for emitting a beam dsigned to exite the molecules at the capillary output, means for detecting the fluorescence of the molecules excited by said beam. The invention also comprises means for generating another electric field, called confinement electric field, which is regularly distributed around said capillaries and which is substantially parallel thereto, said electric field confining the electrophoretic migration field and forcing the molecules to move substantially without divergence in the axis of said capillaries.

14 Claims, 5 Drawing Sheets

FIG_1

FIG_2

FIG_3

FIG_4

FIG. 5

FIG_6a

FIG_6b

FIG_7

FIG_8

MULTIPLE CAPILLARY ELECTROPHORESIS DEVICES WITH DETECTION IN CAPILLARY OUTPUT

The present invention relates to multiple capillary electrophoresis devices.

It is known that conventional gel electrophoresis techniques, in which various samples are injected on a plurality of tracks defined in a gel contained between two plates, are unsatisfactory, given, on the one hand, that they require a certain number of manual operations and, on the other hand, that they do not permit very high migration rates and therefore processing throughputs.

However, major sequencing and genotyping programs require a very high rate of DNA molecule separation and identification.

Electrophoresis techniques are also known which, for migration, use a capillary filled with gel or with another separation matrix having the advantage of being particularly easy to handle, easy to put in and of allowing substantially automatic operation, with higher separation rates than in gel plate electrophoresis by virtue of a strong applicable electric field.

However, the use of a single capillary does not make it possible to achieve the same throughputs as those allowed by electrophoresis techniques using plates which have many tracks in parallel, even though the electric fields that can be applied to a capillary, and therefore the migration rates obtained, are nevertheless higher.

This is why so-called multiple capillary systems have also been proposed, which include a linear array of a plurality of juxtaposed capillaries. In particular, multiple capillary electrophoresis systems have been proposed in which the laser beam for exciting the molecules is directed onto them through the walls of the capillaries, along an axis in the plane of the linear array over which said capillaries are distributed. Said axis is generally perpendicular to the direction in which the capillaries extend, the fluorescence of the molecules being observed using reception means having an optical axis perpendicular to the plane of the linear array of the capillaries.

Reference may, for example, be made in this matter to the publication:
"A Capillary Array Gel Electrophoresis System Using Multiple Laser Focusing for DNA Sequencing"—T. Anazawa, S. Takahashi, H. Kambara—Anal. Chem.—Vol. 68, No. 15,—Aug. 1, 1996—pp. 2699–2704.

However, such a technique is unsatisfactory in view of the detection noise resulting from the interaction between the excitation light and the fluorescence of the walls of the capillary. Further, the laser beam loses intensity as it passes through the capillaries, so that the molecules which lie in the capillaries furthest from the laser source are excited less than those moving through the first capillaries.

In order to solve this problem, it has also been proposed, in particular in:
"Capillary Array Electrophoresis Using Laser-Excited Confocal Fluorescence Detection"—X. Huang, M. Quesada, R. Mathies—Anal. Chem. 1992, 64, 967–972, to use an excitation beam emitted perpendicularly with respect to the plane of the linear array and to carry out detection of the fluorescence using optical means whose axis coincides with that of the beam, this axis and the excitation beam being moved successively in the course of time from capillary to capillary.

But this technique is not satisfactory either, given that it requires complex mechanical means and, further, the movement of the detection means from one capillary to another leads to a great deal of dead time.

Multiple capillary systems are moreover known in which the molecules passing through the capillaries are excited by laser radiation which is directed, just at the output of the linear array, into the plane of said linear array and perpendicular to the direction in which the capillaries extend. The fluorescence of the molecules excited by this radiation is detected using, in particular, a CCD camera which is oriented with an axis perpendicular to the plane of the linear array of capillaries.

A system of this type is, for example, presented in the publication:
"Analysis of Nucleic Acids by Capillary Electrophoresis"—C. Heller—pp. 236 to 254 Editions Vieweg—1997.

Exciting the molecules and detecting the fluorescence outside the capillaries ensures a signal to noise level higher than that accessible in conventional detection layouts, where the excitation and the detection takes place directly through the walls of the capillaries.

However, such a system requires the provision of means preventing the molecules at the output of the various capillaries from diverging too greatly.

This is generally done using laminar buffer flows, which requires, for the cuvette in which the capillaries are accommodated, high-precision mechanical production in glass. In particular, the device will need to be capable of avoiding any gas bubble perturbing the flow.

As will have been understood, such a technique has the major drawback of being very expensive.

Furthermore, it does not allow the operator to handle with ease the capillaries, which require a high degree of alignment precision.

In addition, it requires large volumes of solution which is used for the flows.

What is more, it has been found in practice that this technique is difficult to use except by specialists.

A system for detection at the output of the capillaries without laminar flow, and which avoids these drawbacks, has been proposed by H. Kambara (U.S. Pat. No. 56 67 656 variants 7 and 8). In this system, the detection takes place in the small-dimensioned (0.5 mm) space formed between the electrophoretic separating capillary and a second capillary, which faces the former and is used for passing an electric current. Said detection space is located in an optically favorable buffer-filled cavity. The electric current passes through the detection space between the two capillaries so that the samples migrate from the first capillary to the second. According to the patent of H. Kambara, since the separation between the capillaries is small, these molecules should diverge little in the detection cavity. However, calculations of electrostatics clearly show that, on the contrary, the electric field diverges laterally in the gap between the capillaries. What is more, it found in practice that any system with residual lateral dispersion is inapplicable because it entails resolution losses and contamination between analysis channels. Further, experiments clearly show lateral dispersion of the molecules in the gap between two capillaries, causing loss of analysis resolution. As will have been understood, such a system is not therefore effective. Further, it is difficult to use because it requires precise alignment of capillaries facing one another separated by a small distance.

One object of the invention is therefore to provide a multiple capillary electrophoresis device in which the excitation of the molecules and the detection of their fluorescence are carried out at the output of the capillaries, which does not have the drawbacks of the prior art systems and which is particularly reliable, easy to use, and has a level of performance allowing high-rate sequencing and genotyping.

To that end, the invention provides a multiple capillary electrophoresis device including a plurality of juxtaposed capillaries, means for generating inside the capillaries an electric field which ensures electrophoretic migration, at least one source for emitting a beam intended to excite molecules at the output of the capillary, means for detecting the fluorescence of the molecules excited by said beam, characterized in that it includes means for generating another electric field, referred to as the confinement electric field, which is distributed uniformly around said capillaries and which is substantially parallel to them, this electric field confining the electrophoretic migration field and forcing the molecules to move substantially without diversions in the axis of said capillaries.

Such a device is advantageously supplemented by the various characteristics below, taken individually or in any of their technically feasible combinations:

the device includes at least one intermediate metal electrode directly juxtaposed with the capillaries in the vicinity of their output, as well as a metal electrode which defines the electrophoretic field and which is arranged level with the outputs of the capillaries, parallel to the intermediate electrode and perpendicular to the capillaries, these two electrodes together imposing a confinement electric field at the output of the capillaries;

the potential which is applied to this intermediate electrode is at a value between those of the potentials of the electrodes imposing an electric field between the ends of the capillaries;

it includes a detection cavity in which the capillaries are received at their end, the intermediate electrode being arranged outside this cavity;

the wall of said cavity which faces the intermediate electrode has orifices ensuring electrical contact between said intermediate electrode and the electrode which is arranged level with the outputs of the capillaries;

the capillaries are contiguous, and only one capillary out of two is filled, the electric field at the output of a filled capillary being confined laterally by the confinement electric field at the output of the adjacent unfilled capillaries;

the potential difference applied to the filled capillaries is different from that applied to the unfilled capillaries;

the capillaries are distributed in one or more linear arrays, and in the direction perpendicular to the plane of the linear array(s), the electric field at the output of the capillaries is, further, confined by the geometry of a cavity in which said capillaries are received;

a linear array of capillaries is contained between dielectric plates which, at the output of the capillaries, have a recess and are separated by a distance less than or equal to the external diameter of said capillaries;

it includes, facing the capillaries, a plurality of orifices which are aligned with said capillaries and in which the electric fields at the output of the capillaries in which the molecules migrate are channeled;

the orifices are ends of other capillaries.

BRIEF DESCRIPTION OF THE DRAWINGS

Other characteristics and advantages of the invention will become further apparent from the description below. This description is purely illustrative and nonlimiting. It should be read with reference to the appended drawings, in which.

Figure 1:
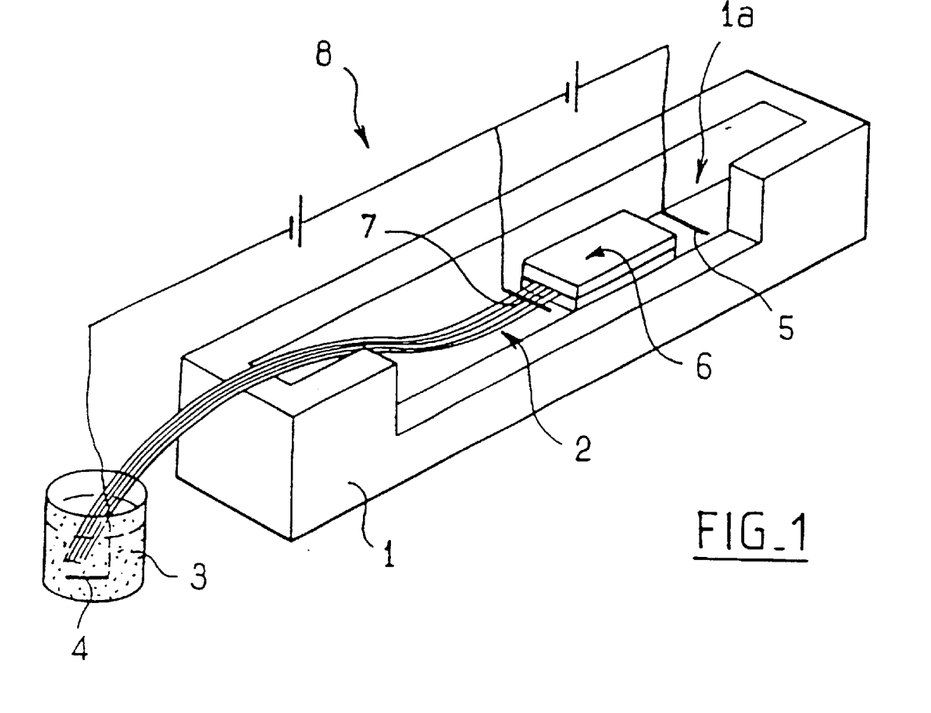
FIG. 1 is a schematic perspective representation with cutaway of a device according to one possible embodiment of the invention.
Figure 2:
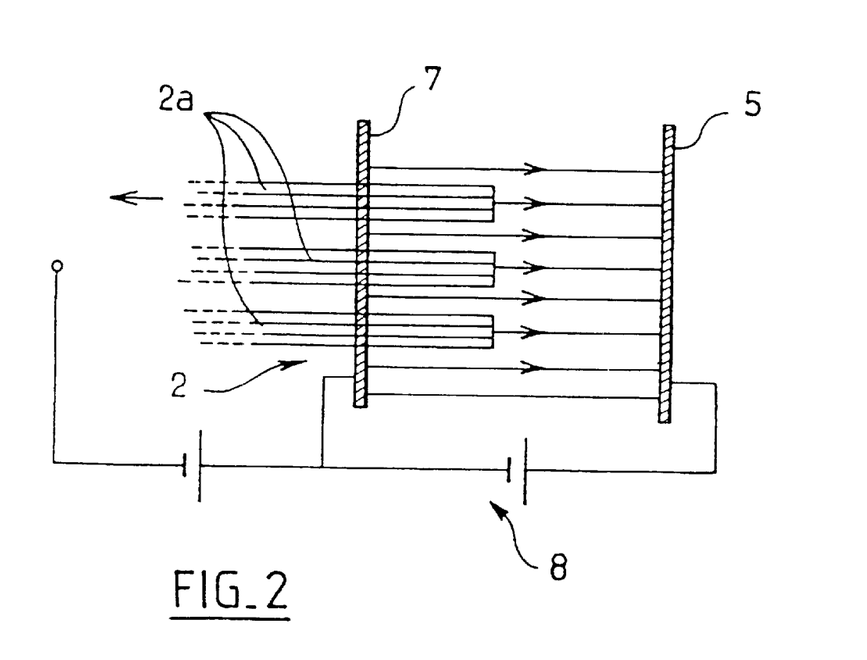
FIG. 2 is a schematic representation in plan view of the confinement configuration of the device in FIG. 1.

The device illustrated in FIGS. 1 and 2 includes:

a container 1 in which a channel 1a is defined, a linear array 2 of capillaries 2a which extents in part through the channel of said container 1, a vessel 3 in which said linear array of capillaries 2 is accommodated at one end and in which a metal cathode 4 is arranged, a metal anode 5 which is arranged in the channel of the container 1 downstream of the other end of the linear array of capillaries 2 and which extends perpendicular to the capillaries, level with them, a detection cavity 6 in which said end of the linear array 2 of capillaries is accommodated, an intermediate electrode 7 which is arranged in the channel of the container 1 upstream of the end of the linear array 2, in the vicinity of this end and which is juxtaposed with the capillaries, means 8 for applying given potential differences between the cathode 4 and the anode 5, as well as between the intermediate electrode 7 and the anode 5.

The channel 1a is filled with a buffer solution of polymers which is identical to that of the electrophoretic separation medium in the capillaries.

The solution filling the channel is advantageously a viscous solution reducing the diffusion of the molecules and convective movements.

The solution filling the channel is advantageously a solution of polymers which prevents electro-osmotic flow, for example a solution in 5% strength poly(vinyl pyrrolidone) buffer.

The solution filling the channel is advantageously filled with a gel or alternatively a thermosensitive solution of polymers which gels at high temperature.

The intermediate electrode 7 is a metal electrode perpendicular to the capillaries of the linear array 2 and parallel to the anode 5.

This electrode 7 is for example a metal wire placed on the linear array 2 of capillaries, transversely to them. As a variant, the electrode 7 may consist of two metal wires of this type, which are arranged transversely on the linear array 2, on either side of it. Also as a variant, it may consist of a metal plate pierced with holes through which the capillaries of the linear array 2 pass. Of course, many other embodiments may also suffice.

The electrodes 5 and 7 are immersed in the solution with which the channel 1a is filled.

The potential which is applied to this intermediate electrode 7 is at a value between that of the potential applied to the anode 5 and that of the potential applied to the cathode 4, so as to generate around the linear array 2 of capillaries an electric field which is distributed uniformly around said linear array 2 and which is substantially parallel to said capillaries.

The intermediate electrode 7 thus makes it possible, with the electrode 5, to generate at the output of the capillaries 2a another electric field which, instead of being divergent as is generally the case, is substantially parallel to the axes of the capillaries, as illustrated by the arrows in FIG. 2 which symbolically represent the direction of the current lines between the electrodes 5 and 7. This electric field is referred to as the "confinement field" because it confines the electrophoretic migration field generated between the electrodes 4 and 5. With the distributions conventionally used for capillaries, in the absence of such a confinement field, the fields at the output of the capillaries diverge strongly: they are equivalent to that of a radial point charge. With the confinement field imposed by the intermediate electrode 7 and the electrode 5, the movement of the molecules being analyzed continues almost linearly beyond the capillaries 2a.

Figure 3:
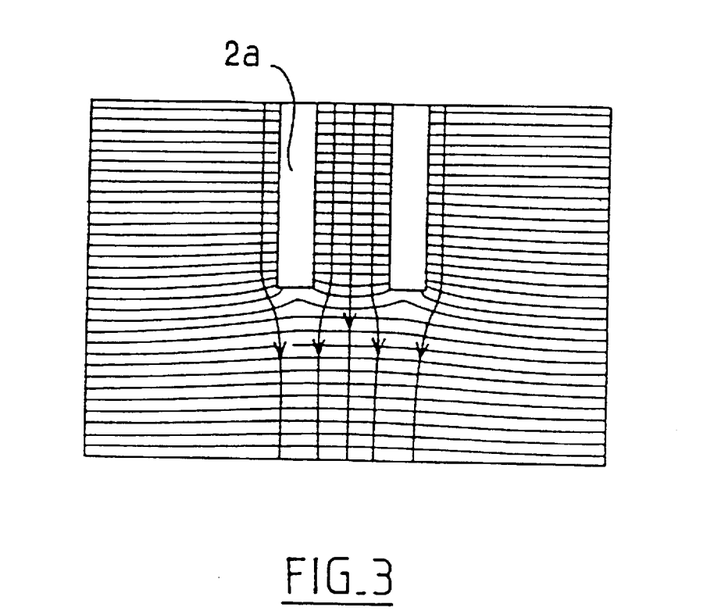
FIG. 3 is a schematic representation in plan view illustrating the current lines along which the molecules leaving the capillary move at the output of a capillary.

More precisely, the value of the potential of the electrode 7 is preferably chosen so that the lines along which the molecules to be analyzed move are, at the output of the capillary 2a, of the type illustrated by the arrows leaving the capillaries in FIG. 3.

The cavity 6 advantageously has a restricted cross section which contributes to the confinement of the field in the direction perpendicular to the linear array 2, and, further, limits the strength of the current of the confinement field and, consequently, the Joule effect which results from it. For example, this cavity 6 is defined by two plates between which the end of the linear array of capillaries is accommodated.

In addition, the electrode 7 is preferably arranged outside the cavity 6, so that the release of gas generated by said electrode do not perturb the detection zone.

The wall of the cavity 6 which faces this intermediate electrode 7 then advantageously has orifices which ensure contact between said electrode 7 and the electrode 5, via the electrolyte solution. These orifices are, for example, holes which have a diameter of the same order of magnitude as those of the capillaries and are interposed between said capillaries.

By way of example, the various constituent elements of the device which has just been described may have the following characteristics.

The container 1 is made of Plexiglass® and has a height of 1 cm, a width of 1.5 cm and a length of 12 cm.

The detection cavity 6 is arranged on the bottom of the channel 1a. It is of rectangular shape and has a cross section matched to that of the linear array 2 of capillaries. It consists of two Teflon® plates which have a thickness equal to the external diameter of the capillaries which are used (360 $\mu$m), and a length substantially equal to 2 cm, are placed on the bottom of the main container and between which spacers are interposed. The width of these spacers (approximately equal to 0.5 cm) is adjusted so that the depth of the cavity corresponds to that of the row of capillaries. A 2 mm-thick glass microscope slide pressed onto the separators is used as a cover for the cavity 6.

The capillaries 2a are coated with polyimide as far as their ends.

The excitation of the molecules in the cavity 6 is carried out at the output of the capillaries 2a using a beam which is perpendicular to the axis of said capillaries and which is either in the plane in which said capillaries 2a are distributed or perpendicular to this plane.

In the first case, the width of the linear array 2 of capillaries is limited by the natural divergence of the laser beam, but all of the beam is utilized for exciting the molecules in all the capillaries.

In the second case, use is for example made of an elliptical beam whose major axis has a length corresponding to the width of the linear array of the capillaries 2a. Only a fraction of the beam is actually used to excite the signal. The detection of the fluorescence may be carried out perpendicularly to the plane of the linear array of the capillaries.

The inventors have tested a device of this type by making fluorescein migrate continuously through it. A laser beam (with a wavelength of 488 nm and emitted with a power of 10 mW) broken up over a width of about 1 cm was focused perpendicularly to the axis of the capillaries, at an adjustable distance from the ends.

The fluorescent light was collected using a photographic apparatus fitted with a macro objective and a SCHOTT colored filter blocking the laser light, placed vertically in line with the detection zone.

For this experiment, the capillaries 2a were inserted 1.5 cm inside the detection cavity 6; the intermediate electrode 7 was a single electrical wire with a diameter of 1 mm and placed at 2 cm from the ends (outside the cavity 6) and simply pressed against the capillaries 2a; the anode 5 was an identical wire placed facing the capillaries 2a, outside the detection cavity 6, at 2 cm from the ends. The electrodes 4, 5 and 7 were in electrical contact through the polymer solution (hydroxypropyl cellulose at a strength of 0.5% in solution in TBE 0.1X buffer) which fills the cavity 6 and the capillaries 2a.

The configuration was electrically powered by two supplies in series: a first, high-voltage stage between the cathode 4 at the input of the capillaries 2a and the electrode 5 provided the potential difference in the capillaries 2a for the electrophoretic migration (corresponding to a field of 35 to 70 V/cm); a second, lower-voltage stage, between the intermediate electrode 7 and the anode 5, imposes the electric field in the detection cell constituted by the cavity 6 (a field of the order of 75 V/cm).

The potential of the intermediate electrode 7 was set to ground.

It was found that the currents output by the capillaries 2a were confined and that the bands at the output of the capillaries 2a were separated. These bands are increasingly confined as the external field becomes stronger.

Embodiments other than that which has just been described may, of course, be envisaged.

In particular, it is in fact possible, in a reduced geometry, to confine the field lines leaving the capillaries without intermediate electrode by filling one capillary out of two with samples to be analyzed.

Figure 4:
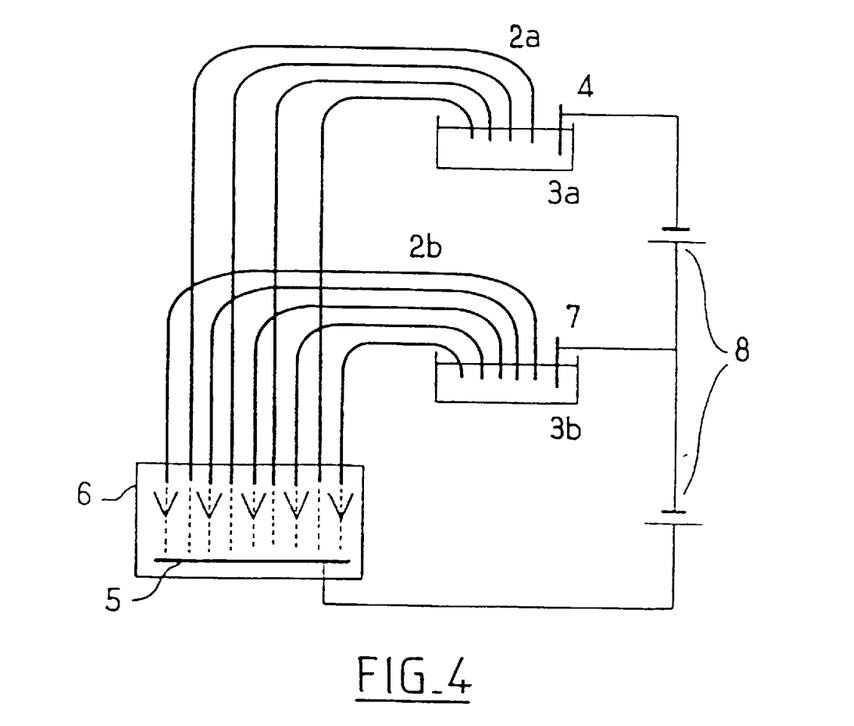
FIG. 4 is a schematic representation of another possible embodiment of the invention.

This is what has been illustrated in FIG. 4, on which the filled capillaries have been referenced by 2a, whereas the capillaries not filled with samples to be analyzed have been referenced by 2b.

At their opposite end from the detection cavity 6, the capillaries 2a are immersed in a cathode vessel 3a, while the capillaries 2b are immersed in a cathode vessel 3b.

The cathode vessel 3a receives an electrode 4 which, with the anode 5 immersed in the detection a cavity 6, generates an electrophoretic migration field inside the analysis capillaries 2a.

The cathode vessel 3b receives an electrode 7 which is at a potential intermediate between that of the cathode 4 and that of the anode 5.

In FIG. 4, the two sources making it possible to apply the potential differences between the electrode 4 and the electrode 7, on the one hand, and the electrode 7 and the electrode 5, on the other hand, have been referenced by 8.

The capillaries 2a and 2b have thicknesses and internal diameters which are small enough so that, when said capillaries 2a, 2b are arranged contiguously, the lateral broadening of the field is limited by the interaxial distance between said capillaries. The molecules output by a capillary 2a, which follow the field lines, are isolated from those of the other capillaries 2a by the confinement field lines at the output of the adjacent capillaries 2b. This is what has been illustrated in FIG. 5.

Figure 5:
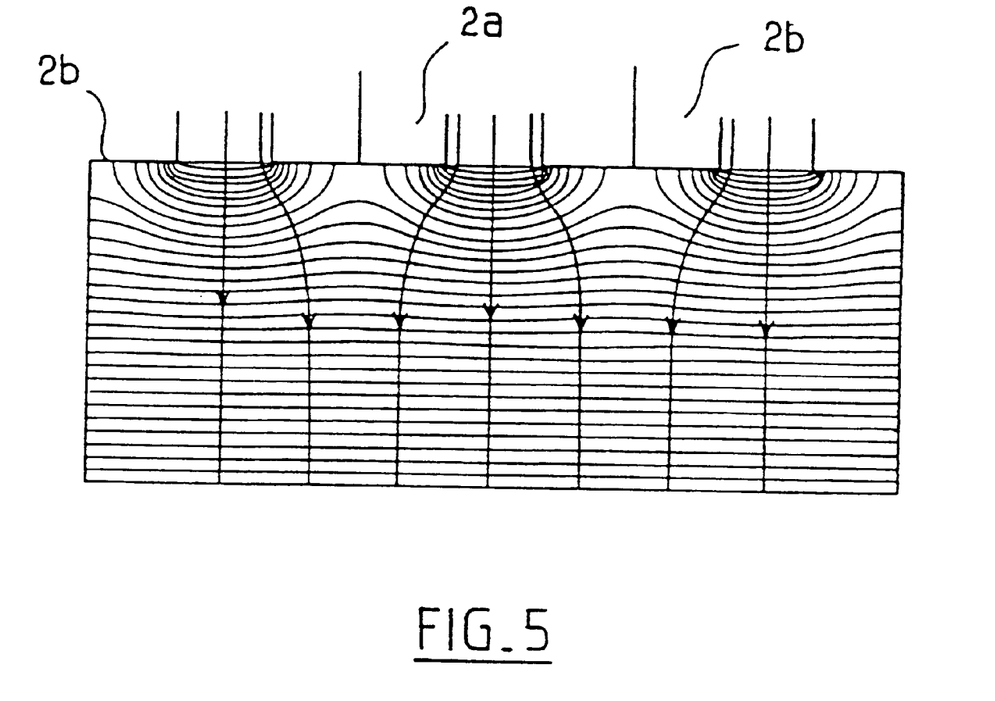
FIG. 5 is a representation similar to that in FIG. 3 illustrating another possible embodiment of the invention.

In this configuration, the thickness of the walls of said capillaries 2a, 2b is preferentially less than their internal diameter.

As a variant, the capillaries 2b not filled with samples may have an internal or external diameter or a length different than those of the analysis capillaries 2a.

As will also have been understood, the electric field in the unfilled capillaries 2b may be different than that in the analysis capillaries 2a.

In the direction perpendicular to the plane of the linear array of capillaries, the broadening may be limited by a narrow geometry of the detection cavity 6, matched to the diameter of the capillaries 2a. This is what has been illustrated in FIGS. 6a and 6b, which illustrates a configuration in which the linear array 2 of capillaries 2a is held between plates 9 of dielectric materials, said plates 9 extending beyond said capillaries.

Figure 6A:
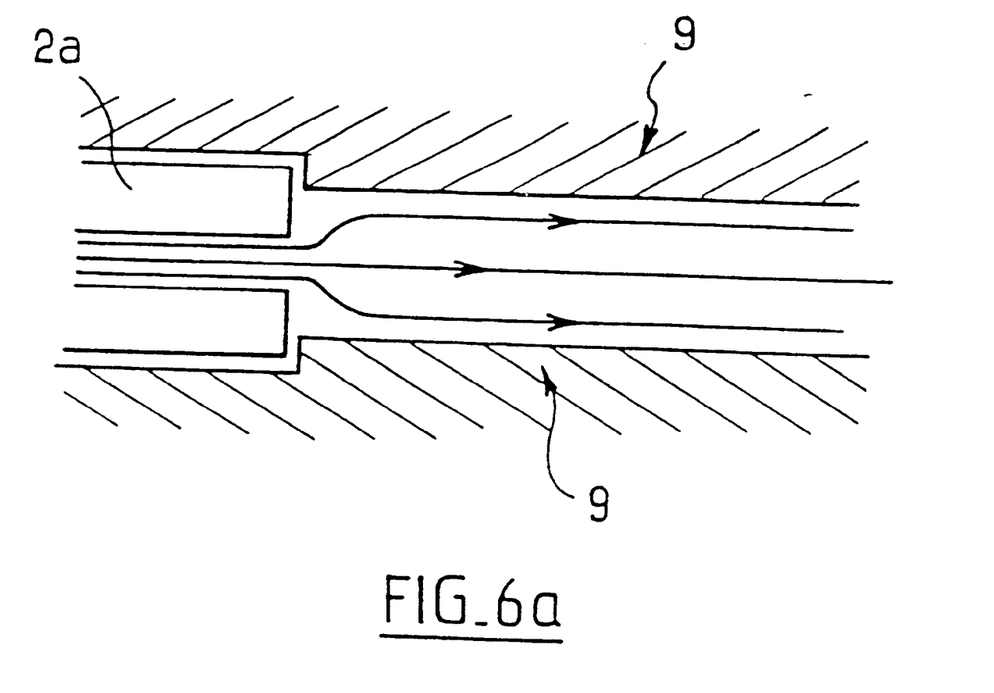
FIGS. 6a and 6b are schematic representations in axial and cross-sectional view illustrating the means used to produce confinement in the direction perpendicular to the plane of a linear array of capillaries with a device of the type illustrated in FIG. 5.
Figure 6B:
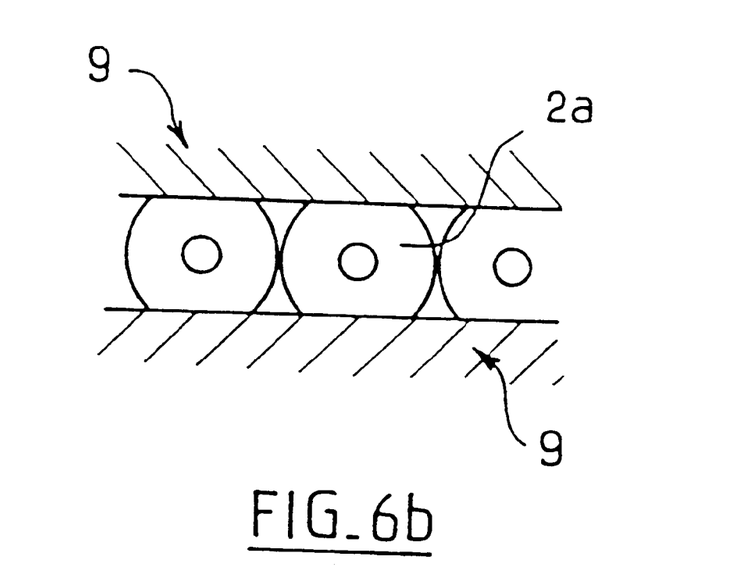

The distance between the plates 9 is preferentially less than or equal to the external diameter of the capillaries. To that end, the plates 9 have a recess at the output of the capillaries.

Figure 7:
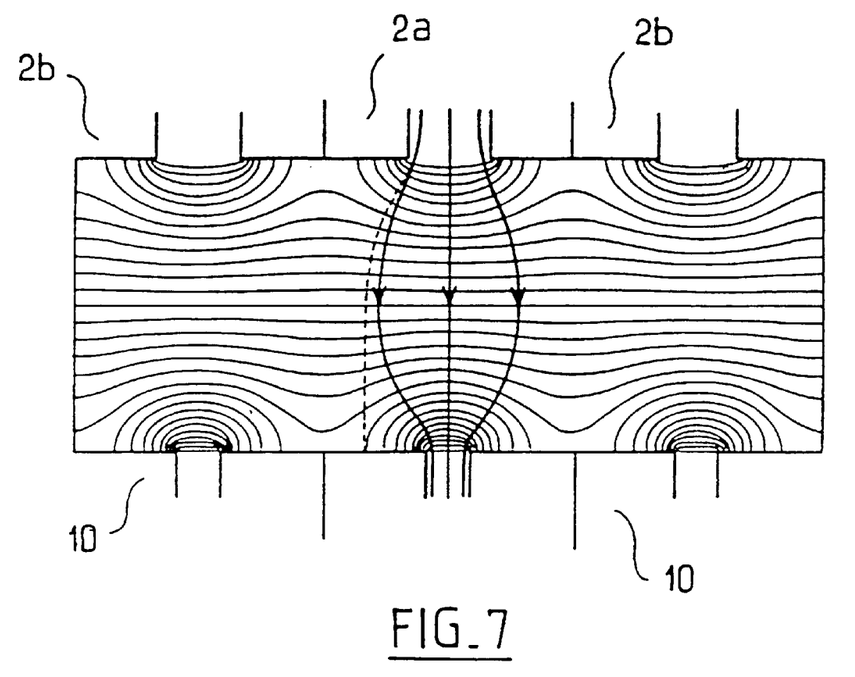
FIGS. 7 and 8 are schematic representations similar to those in FIGS. 3 and 5 illustrating other embodiments of the invention which are also possible.

Provision may further be made for the ends of the electrophoretic separation capillaries 2a to face a series of orifices in which the electric field is channeled, it being advantageously possible for these orifices to consist of capillaries 10 placed in alignment with the capillaries 2a (FIG. 7).

The current lines are then confined further.

Figure 8:
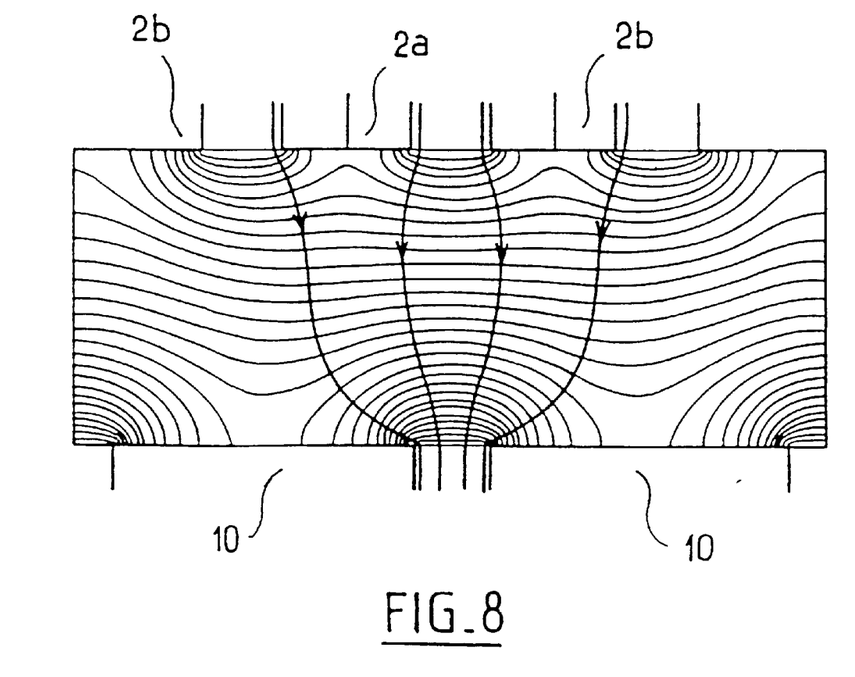

This configuration can be reinforced yet more by arranging capillaries 10 only facing the filled capillaries 2a. As illustrated by FIG. 8, this configuration makes it possible to channel in the capillaries 10 the field lines from the filled capillaries 2a and intermediate capillaries 2b.

The devices which have been described have many advantages over the detection devices without capillaries known to date, and in particular over laminar flow devices.

In particular, they have high sensitivity and permit a large dynamic range of detection.

They are very easy to use.

They also make it possible to immerse the capillaries in viscous solutions of polymer, while the capillary flow techniques require capillaries filled with gel and a buffer flow.

Further, the proposed devices allow the capillaries to be filled with ease, it being possible for the viscous solution of polymer to be injected from the output container, once the capillaries are in place.

In addition, the samples may be introduced therein by hydraulic pressure, while in laminar flow devices, only electrokinetic injection is possible.

The device provided by the invention also allows greater tolerance in terms of the alignments of the capillaries. Manufacture of the devices is simplified.

Lastly, the structures which have just been described have the advantage of being able to be used with capillaries distributed as a matrix, in a plurality of superposed linear arrays.

What is claimed is:

1. Multiple capillary electrophoresis device including:
   a plurality of juxtaposed capillaries (2a),
   means (4, 5) for generating inside the capillaries (2a) a first electric field which ensures electrophoretic migration by an electrophoretic migration field,
   at least one source for emitting a beam intended to excite molecules at the output of the capillary,
   means for detecting the fluorescence of the molecules excited by said beam,
   characterized in that the device includes means (5, 7) for generating a second electric field, referred to as a confinement electric field, distributed uniformly around said capillaries and substantially parallel to them, the second electric field confining the electrophoretic migration field and forcing the molecules to move substantially without diversions in the axis of said capillaries (2a),
   further characterized in that the means (5, 7) for generating the confinement field includes at least one intermediate metal electrode (7) directly juxtaposed with the capillaries (2a) and arranged across the capillaries (2a), in the vicinity of the outputs of the capillaries, the means (5, 7) further including a metal electrode (5) which defines the first electric field and said metal electrode (5) arranged level with the outputs of the capillaries (2a), parallel to the intermediate metal electrode (7) and perpendicular to the capillaries (2a),
   wherein the intermediate metal electrode (7) and the metal electrode (5) impose said second electric field at the output of the capillaries (2a).

2. Device according to claim 1, characterized in that the potential which is applied to this intermediate electrode is at a value between those of the potentials of the electrodes imposing the first electric field between the ends of the capillaries (2a).

3. Device according to claim 1, characterized in that it includes a detection cavity (6) in which the capillaries are received at their output ends, the intermediate electrode (7) being arranged outside this cavity.

4. Device according to claim 3, characterized in that a wall of said cavity (6) which faces the intermediate electrode (7) has orifices ensuring electrical contact between said intermediate electrode (7) and the metal electrode (5) which is arranged level with the outputs of the capillaries.

5. Device according to claim 1, characterized in that the capillaries (2a) are distributed in at least one linear array, and in that in the direction perpendicular to the plane of the linear array, the electric field at the output of the capillaries (2a) is, further, confined by the geometry of a cavity in which said capillaries (2a) are received.

6. Device according to claim 5, characterized in that a linear array of capillaries is contained between dielectric plates which, at the output of the capillaries, have a recess and are separated by a distance less than or equal to the external diameter of said capillaries.

7. Device according to claim 1, characterized in that it includes, facing the capillaries (2a), a plurality of orifices (10) which are aligned with said capillaries and in which the electric fields at the output of the capillaries (2a) in which the molecules migrate are channeled.

8. Device according to claim 7, characterized in that the orifices are ends of other capillaries (10).

9. A multiple capillary electrophoresis device comprising:
   a plurality of capillaries, each capillary comprising a proximal end and a distal end;
   a vessel in fluid communication with the proximal end of each of the capillaries;
   a first electrode in the vessel;
   a container in fluid communication with the distal end of each of the capillaries;
   a second electrode in the container;
   a third electrode in the container distal to the first electrode and proximal to the second electrode;
   wherein the first and second electrodes are adapted to create a first electric field which ensures electrophoretic migration through the capillaries;
   further wherein the second and third electrodes are adapted to create a second electric field referred to as a confinement electric field, distributed uniformly around the capillaries and substantially parallel to the capillaries, the second electric field confining the first electric field;
   further wherein the third electrode is directly juxtaposed with the capillaries and arranged across them, in the vicinity of the distal end of each of the capillaries.

10. The device according to claim 9, wherein a potential which is applied to the third electrode is at a value between a potential of the first electrode and a potential of the second electrode.

11. The device of claim 9, further comprising a detection cavity in which the distal end of each capillary is received, wherein the third electrode is arranged outside the cavity.

12. The device of claim 9, wherein the detection cavity further comprises a wall which faces the third electrode, wherein the wall comprises a plurality of orifices ensuring electrical contact between the third electrode and the second electrode.

13. The device of claim 9, wherein the capillaries are distributed in at least one linear array.

14. The device of claim 13, wherein the at least one linear array comprises a first linear array, further comprising a second linear array of capillaries contained between dielectric plates, wherein the second linear array of capillaries comprises a proximal end and a distal end, wherein the proximal end of the second linear array of capillaries is adjacent to the distal end of the first linear array of capillaries.

* * * * *